United States Patent [19]
Chitayat

[11] Patent Number: 6,137,195
[45] Date of Patent: *Oct. 24, 2000

[54] ROTARY-LINEAR ACTUATOR

[75] Inventor: Anwar Chitayat, Fort Salanga, N.Y.

[73] Assignee: Anorad Corporation, Hauppauge, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/668,705

[22] Filed: Jun. 24, 1996

Related U.S. Application Data

[63] Continuation-in-part of application No. 08/481,239, Jun. 6, 1995, abandoned.
[60] Provisional application No. 60/015,705, Mar. 28, 1996.
[51] Int. Cl.[7] .............................. H02K 33/12; F16C 39/06
[52] U.S. Cl. .......................... 310/12; 310/90.5; 310/156; 310/266; 310/15
[58] Field of Search ...................................... 318/115, 135; 310/12, 13, 15, 14, 27, 34, 35, 36, 154, 156, 90.5, 266; 417/415

[56] References Cited

U.S. PATENT DOCUMENTS

| | | | |
|---|---|---|---|
| 2,722,617 | 11/1955 | Cluwen et al. | 310/266 |
| 3,394,295 | 7/1968 | Cory | 310/12 |
| 3,441,819 | 4/1969 | Palmero | 310/12 |
| 3,777,292 | 12/1973 | Fulenwider | 310/12 |
| 3,851,196 | 11/1974 | Hinds | 310/12 |
| 3,969,042 | 7/1976 | Bächler | 415/354 |
| 4,602,848 | 7/1986 | Honds et al. | 310/12 |
| 4,607,197 | 8/1986 | Conrad | 310/12 |
| 4,626,749 | 12/1986 | Asakawa | 310/12 |
| 4,644,205 | 2/1987 | Sudo et al. | 310/90.5 |
| 4,742,286 | 5/1988 | Phillips | 318/640 |
| 4,808,892 | 2/1989 | Dreibelbis | 310/12 |
| 5,142,172 | 8/1992 | Horikoshi et al. | 310/12 |
| 5,334,892 | 8/1994 | Chitayat | 310/12 |
| 5,397,212 | 3/1995 | Watanabe et al. | 310/90.5 |

*Primary Examiner*—Nestor Ramirez
*Assistant Examiner*—Burt Mullins
*Attorney, Agent, or Firm*—John M. Miller; John J. Horn; William R. Walbrun

[57] ABSTRACT

An actuator, with two independent degrees of freedom, rotates a stage about an axis and moves the stage along the axis, the range of motion defining a cylinder or cylindrical section. The stage is mounted on a hollow cylindrical plunger fitting in an annular well. A bearing allows the plunger to move axially and rotationally, in the preferred embodiment the bearing is an air bearing. The plunger has an array of permanent magnets on its external cylindrical face opposite coils in the well. Equal numbers of oppositely-polarized permanent magnets are arranged in a regular cylindrical pattern at 50% packing density forming rings and columns of like-polarity magnets, the rings of one polarity alternating with rings of opposite polarity and the columns of one polarity alternating with columns of opposite polarity. A set of Z-axis coils (for axial movement) curve around the plunger and are shaped to allow a current in them to produce an axial force with respect to the rings of magnets. A set of $\phi$-axis coils (for rotational movement) have longitudinal axes that are parallel to the axis of the plunger and are sized to allow current in them to impel the columns of magnets. Part of the external surface of the plunger has a grid scale, which is encoded by Z-axis and $\phi$-axis optical pickups to provide position information to a controller.

2 Claims, 13 Drawing Sheets

ROTARY-LINEAR ACTUATOR

This application is based on provisional application Ser. No. 60/015,705 filed Mar. 28, 1996 and a continuation-in-part of U.S. application Ser. No. 08/481,239, filed Jun. 6, 1995 which is now abandoned.

BACKGROUND OF THE INVENTION

The present inventions relates to devices known variously as traversing machines, actuators, motors, positioning devices, robots, etc. More particularly, the invention relates to such devices that rotate an operating stage and move it linearly along an axis of rotation.

Various kinds of robotic actuators are known that provide multiple degrees of freedom. There is a need in the field for actuators that provide high accuracy, low weight, large load-carrying capacity, compact size, smooth operation, and cost-effectiveness. One known type of actuator that provides two-degrees of freedom, which scores highly in terms of the above design goals, is an entire class of so-called X-Y traversing systems, for example, as described in U.S. Pat. No. 5,334,892, the entirety of which is incorporated herein by reference. This patent describes a traversing system with a movable stage supported on an air bearing above a planar base. The traversing system described in the patent is, however, limited to movement in a plane.

OBJECTS AND SUMMARY OF THE INVENTION

An object of the present invention is to provide a actuator that provides independent rotational and axial movement of a stage.

Another object of the present invention is to provide an actuator that is simple in design and construction.

Another object of the present invention is to provide an actuator that is compact and light in weight.

Yet another object of the present invention is to provide an actuator that is cost-effective to manufacture and maintain.

Yet another object of the present invention is to provide an actuator capable of supporting large loads.

Briefly, an actuator, with two independent degrees of freedom, rotates a stage about an axis and moves the stage along the axis, the range of motion defining a cylinder or cylindrical section. The stage is mounted on a hollow cylindrical plunger fitting in an annular well. A bearing allows the plunger to move axially and rotationally, in the preferred embodiment the bearing is an air bearing. The plunger has an array of permanent magnets on its external cylindrical face opposite coils in the well. Equal numbers of oppositely-polarized permanent magnets are arranged in a regular cylindrical pattern at 50% packing density forming rings and columns of like-polarity magnets, the rings of one polarity alternating with rings of opposite polarity and the columns of one polarity alternating with columns of opposite polarity. A set of Z-axis coils (for axial movement) curve around the plunger and are shaped to allow a current in them to produce an axial force with respect to the rings of magnets. A set of φ-axis coils (for rotational movement) have longitudinal axes that are parallel to the axis of the plunger and are sized to allow current in them to impel the columns of magnets. Part of the external surface of the plunger has a grid scale, which is encoded by Z-axis and φ-axis optical pickups to provide position information to a controller.

According to an embodiment of the present invention, there is provided, a rotary-linear actuator, comprising: first and second elements, each having a common axis, the first element having at least one magnet, the second element having at least first and second electrical coils capable of generating respective first and second magnetic fields, a bearing to support the first element with respect to the second element to allow the first and second elements to rotate about an axis relative to each other and to slide in a direction collinear with the axis, the first and second coils being positioned relative to each other and relative to the magnet such as to produce a substantial motive force capable of both rotating and displacing the first and second elements with respect to each other when the first and second coils are excited by an electrical current.

According to another embodiment of the present invention, there is provided, a rotary-linear actuator, comprising: a base element having one of a plurality of magnets and a plurality of coils, a stage element having the other of a plurality of magnets and a plurality of coils, the stage element being connected to the base element such that the stage element is free to rotate on an axis and slide along the axis, the plurality of magnets and the plurality of coils being arranged to generate a motive force therebetween when the plurality of coils is energized.

According to still another embodiment of the present invention, there is provided, a rotary-linear actuator, comprising: a base member, a stage member, the base member having a first cylindrical surface, the stage member having a second cylindrical surface, the first and second cylindrical surfaces having a common axis, the base having one of a plurality of magnets and a plurality of electric coils shaped in such a way as to define a first cylinder coaxial with the common axis and the stage having another of the plurality of magnets and the plurality of electric coils shaped in such a way as to define a second cylinder coaxial with the common axis.

According to still another embodiment of the present invention, there is provided, a rotary-linear actuator, comprising: first and second members, each having a common axis, the first member having at least one first means for generating a first magnetic field, the second element having at least second and third means for generating second and third magnetic fields, means for supporting the first member with respect to the second member such that the first and second members are free to rotate about an axis relative to each other and to slide in a direction collinear with the axis, the second and third means for generating being positioned relative to each other and relative to the magnet such as to produce a substantial motive force capable of both rotating and displacing the first and second elements with respect to each other.

According to still another embodiment of the present invention, there is provided, a rotary-linear actuator, comprising: a first member with a cylindrical opening, a second member, cylindrical in shape, sized to fit within the annular cylindrical opening, the first and second members being connected by a bearing means for maintaining concentricity of the first and second members and freedom of relative linear movement of the first and second members along, and relative rotation of the first and second members about, a common axis of the first and second members, the first member having a means for generating a first magnetic field characterized by a first pattern, the second member having a means for generating a second magnetic field characterized by a second pattern, one of the first and second patterns being regular and permanent, the first and second magnetic fields being configured to interact so as to produce a motive force causing the first and second members to move relative to each other, another of the first and second patterns being time-varying, such that the first and second members are impelled to move continuously in rotational and linear modes.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

Figure 6A:
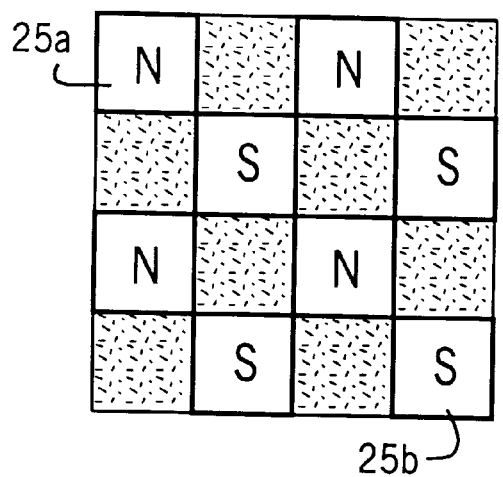
FIG. 6a shows a planar projection of the magnet array attached to the plunger element or a base according to one embodiment of this feature of the invention.

Referring to FIGS. 1a, 1b, 6a–6c, and 7a, in an embodiment of the invention, a cylindrical plunger element 26 floats on an air bearing 76 in a well formed by a motor support 27 and an air bearing support 28. A surface defining the well has a groove 16 through which air is distributed to form air bearing 76. Appropriate orifices and pockets (not shown) are supplied as required according to known techniques for making air bearings. Plunger element 26 is free to move axially and rotate about its axis supported on air bearing 76. Plunger element 26 has an array of magnets 25 covering an outside surface thereof. Half of magnets 25 are oriented so that their north poles point radially outward and an equal number are oriented so that their north poles point radially inward. Referring momentarily to FIG. 6a, a flat projection of the arrangement of magnets 25 shows their relationship to each other. Magnets 25 include outward-oriented magnets 25a and inward oriented magnets 25b arranged in a regular pattern to form rings and columns of magnets. In the rotary-linear actuator, the arrangement shown in FIGS. 6a would be projected on the cylindrical surface of plunger element 26 to form the cylindrical array shown in FIG. 7a. In this arrangement, rings of one polarity alternate with rings of opposite polarity and columns of one polarity alternate with columns of opposite polarity.

Figure 4A:
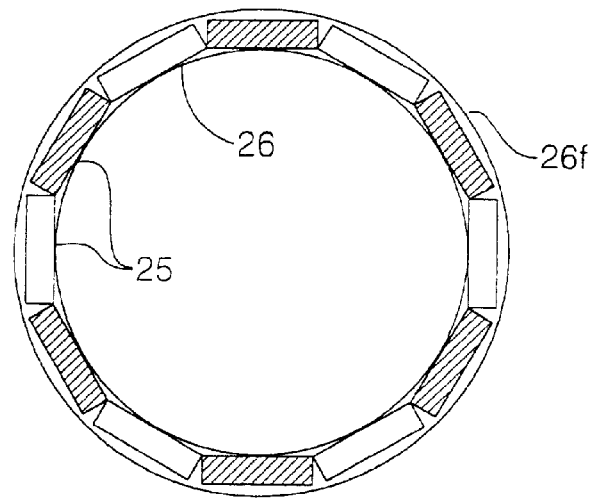
FIG. 4a is a cross section through an axis of the embodiments of FIGS. 1a and 1b in a preliminary stage of manufacture showing magnets arranged about a central plunger element.
Figure 4B:
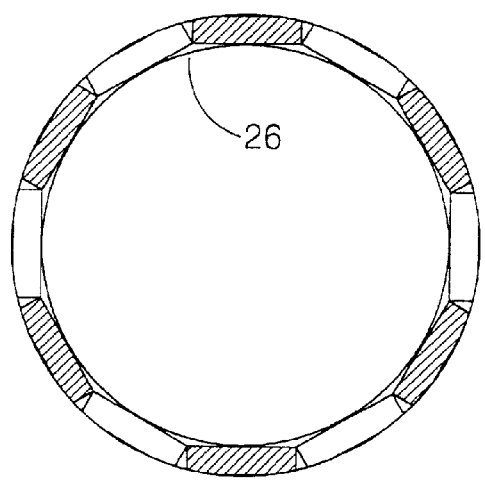
FIG. 4b is a cross section of the plunger of FIG. 4a in a further stage of manufacture showing magnets coated with epoxy after grinding to form a cylindrical outer surface.
Figure 4C:
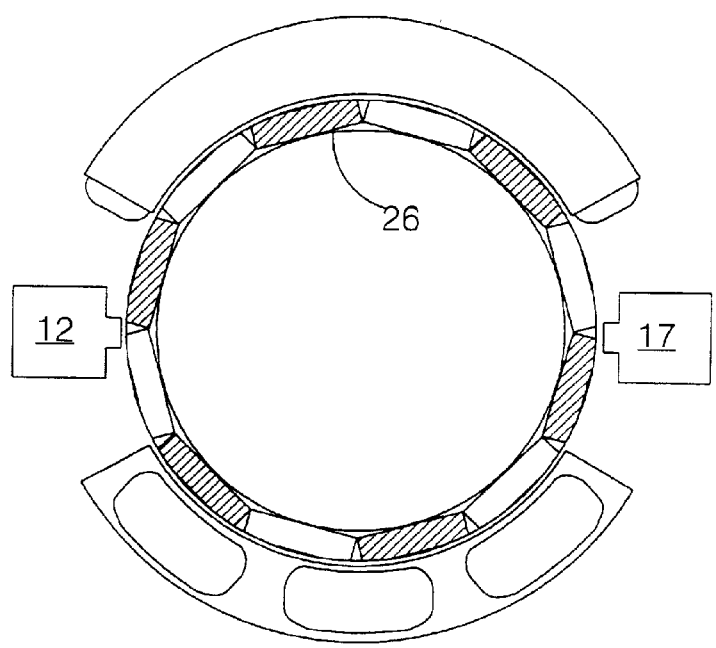
FIG. 4c is a cross section of plunger element according to an embodiment of the invention showing the arrangement of z and φ motors and optical pickups.
Figure 7A:
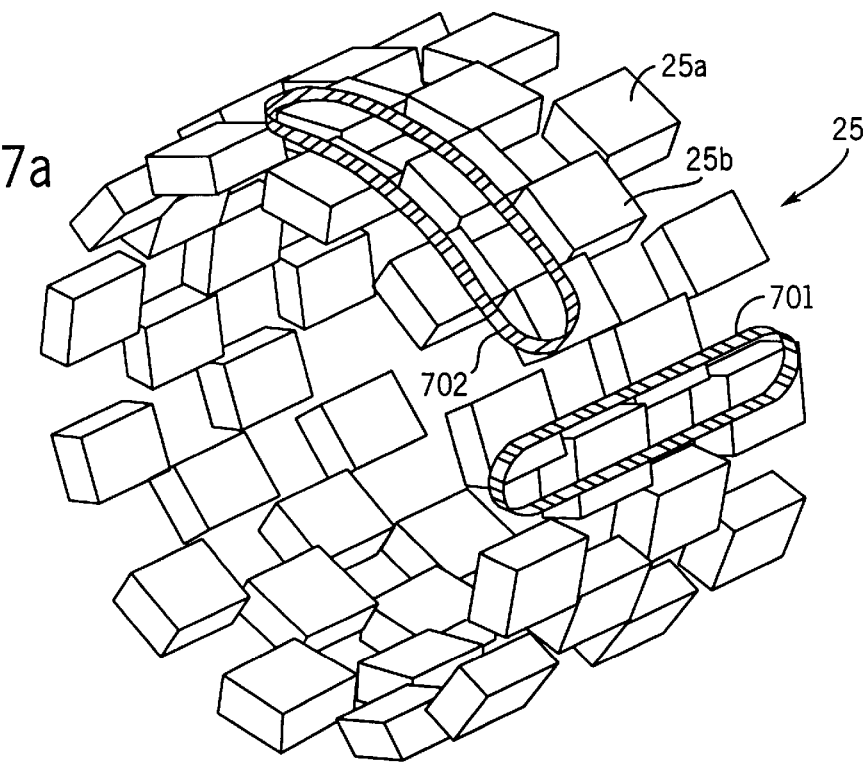
FIG. 7a shows the arrangement of magnets relative to z and φ coils of z and φ motors for the cylindrical plunger element of the invention.
Figure 7B:
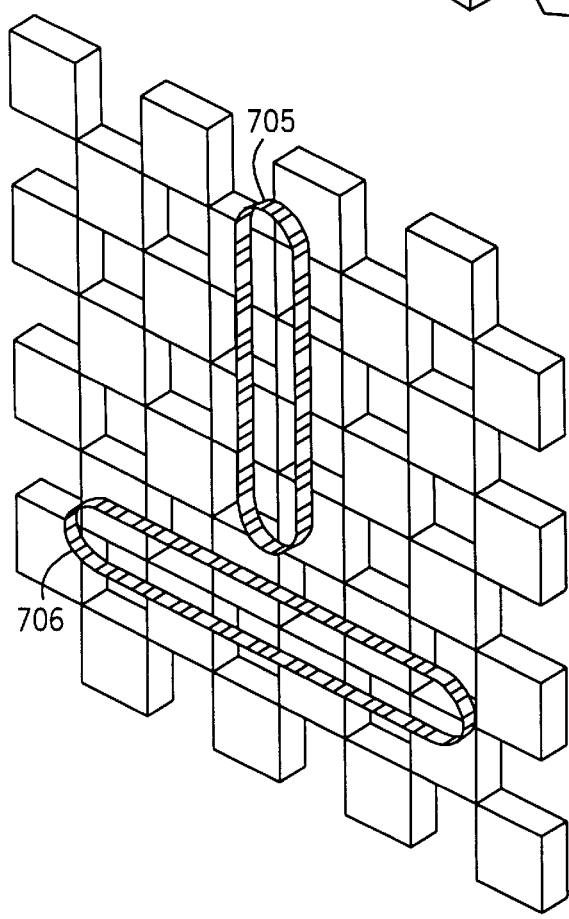
FIG. 7b shows the arrangement of magnets relative to x and y coils of x and y motors of an analogous planar x-y positioning system.

Referring also to FIG. 4c, a set of z-axis coils (for axial movement) curve around the plunger. Z-axis coils 15a are shaped to allow a current in them to create an axial force on the magnets. A set of φ-axis coils 15b (for rotational movement) have longitudinal axes that are parallel to the axis of the plunger and are sized to allow current in them to generate a tangential force on the columns of magnets. Air is injected into a space between a center column defining the center of the annular well and the internal surface of the plunger to support the plunger. Plunger element 26 is driven in rotational and linear modes, respectively, by z motor 45 and φ motor 46. Both z and φ motors 45 and 46 contain coils that generate changing fields that interact with the fields generated by magnets 25 to generate a motive force on plunger element 26. In FIG. 7a, positions of coils 701 of φ motor 46 and coil 702 of z motor 45 are shown schematically relative to magnets 25. FIG. 7a shows only one coil per mode for purposes of explanation. In reality, a motor may consist of several coils. In addition, the number of magnets shown in FIG. 7a is chosen for clarity, the actual density and size would be chosen based on the application. For a practical device, many more or fewer magnets could be used, depending on the resolution and size of the actuator required for the application. In addition, the lengths and widths of coils 701 and 702 may differ substantially from that shown in FIG. 7a. Typically, 3 phase coils are used separated 120 degrees apart to provide smooth transition between phases. In the present invention, a single phase, two phase, or three-phase configurations can be used, depending on the application.

A preferred configuration consists of 10 to 16 magnets per ring of magnets. That is, for a ring of twelve magnets, when the pattern of FIG. 6a is used, there would be six magnets of one pole orientation encircling the plunger below which there would be 6 more magnets. Each magnet is separated from the others by a gap one magnet-width wide. For example, the configuration of FIG. 7a has 12 magnets per ring. This would leave enough room for the coil ends and the encoders.

Figure 1A:
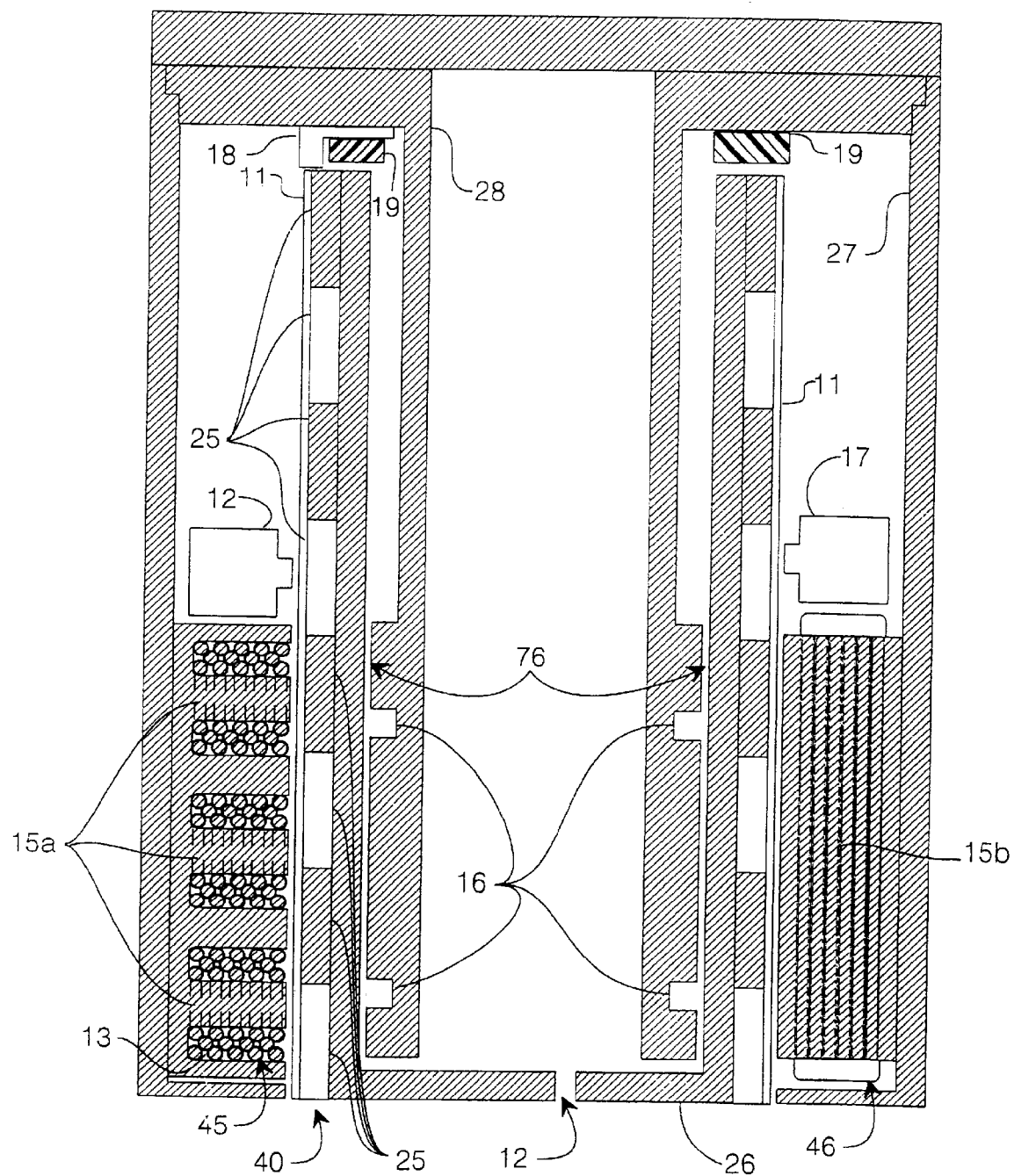
FIG. 1a is a cross-section of a rotary-linear actuator, according to an embodiment of the invention, in which a plunger is shown in a substantially retracted position.

In FIG. 1a, z motor 45 and φ motor 46 have coils 15a and 15b embedded in laminations 13. The laminations can be manufactured from thin sheets of steel laminated together or from compacted powdered metal depending on the application and speed.

The coils can be manufactured by winding the coils in a standard manner, using copper wire surrounded by a heat-actuated glue. The z-axis coils curve around the plunger. Initially, the coils can be formed in a straight longitudinal configuration. Then, a current may be applied to the coils and the coils bent in a jig or mold to the proper shape. After the coils cool, they retain their curved shape. The coils can then be inserted in slots in the laminations and varnish or epoxy applied to the coils and laminations. Voids may be filled with epoxy. The surface adjacent the plunger can then be machined appropriately to form a surface with the proper dimensions.

In an alternative embodiment, the coils can be made in the same manner as described immediately above, except that, instead of using laminations, a powder iron, held together with glue or epoxy may be used. In such a material, the iron particles are small and insulated from each other, a high volume resistivity is obtained to minimize the generation of eddy currents. This configuration has the advantages of low cost and ease of manufacture. It has, however, the disadvantage of lower flux density.

Another configuration for the coils is to employ coils embedded in resin, only. No iron or steel is used in order to eliminate eddy currents and reduce cogging. This configuration is discussed in U.S. patent application Ser. No. 08/346,860, the entirety of which is incorporated herein by reference. This configuration is known (Anorad's LE type motor) and a design optimized around this configuration of the coils is described below with reference to FIGS. 3a–3b.

Note that although according to the above embodiments, the magnets and coils are shown lying immediately beneath smooth surfaces on the stage and base elements of the rotary-linear actuator, this is only one of other possible configurations. For example, the magnets and coils could be formed on a mold and the voids left unfilled. This would present a rough surface, but would still be operable and would avoid the machining required by the method described above.

Figure 5A:
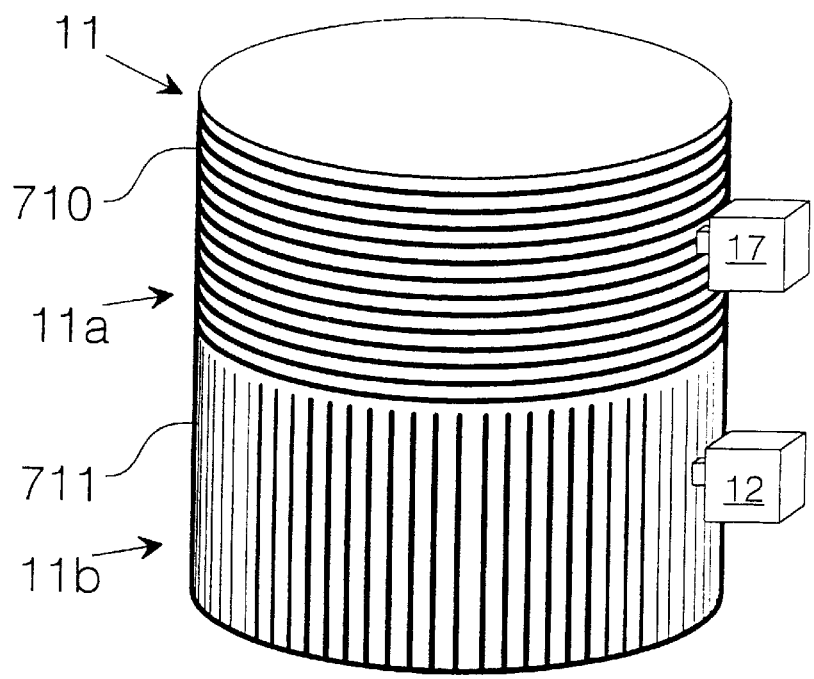
FIG. 5a shows a simplified view of plunger element with z and φ encoders in an embodiment in which the z scale and φ scale are formed on separate portions of the plunger.
Figure 5B:
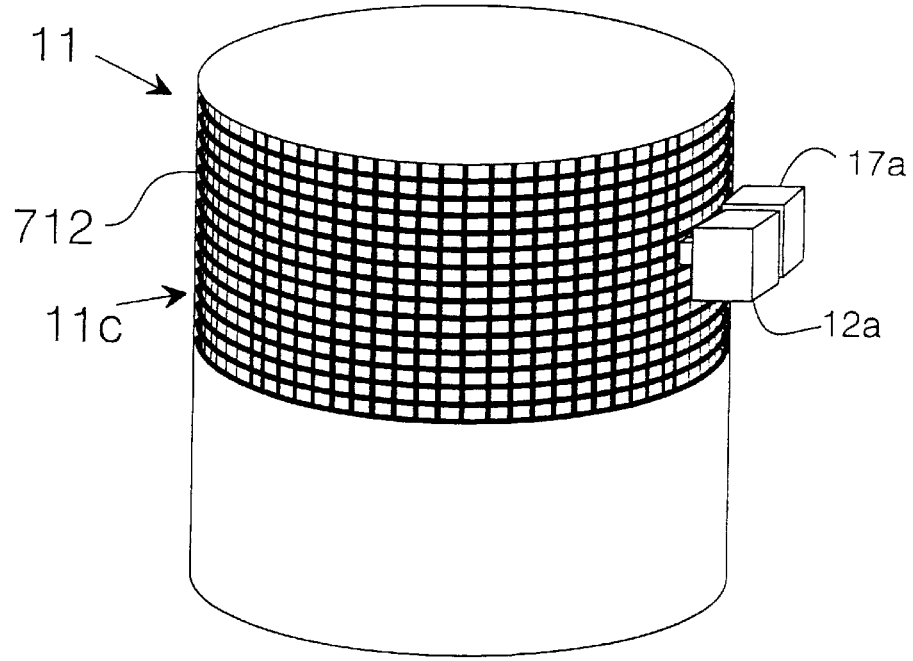
FIG. 5b shows a simplified view of plunger element with a grid scale that is scanned by both z and φ encoders.

Referring to FIGS. 1a, 1b, 5a, and 5b, affixed to the surface of magnets 25, is a thin sheet carrying an encoder scale 11. Encoder scale 11 is etched with a pattern of reflective and non-reflective regions that are scanned by optical pickups 12 and 17 to register movement of plunger element 26. As shown in FIGS. 5a and 5b, encoder scale 11 can be formed as separate linear scales 11a and 11b or combined into one grid scale 11c. When the scales are separate, optical pickups 12 and 17 operate in the conventional way. In addition, when using the configuration of scale 11a, optical pickups 12 and 17 must be arranged as shown in FIG. 5a or another appropriate way so that they "see" the appropriate scale throughout the positioning range. Thus, a different arrangement of optical pickups 12 and 17 would be required from that shown in FIGS. 1a and 1b. When the scales are combined as for grid scale 11b shown in FIG. 5b, optical pickups 12a and 17a are somewhat different from the conventional linear design. Optical pickup 12a, for example, projects light at, and senses reflected light from, an elongated detection region with a horizontal axis. The elongated detection region wraps partially around the cylindrical surface of scale 11 so that a ring of reflective and non-reflective patches are subtended. When plunger element 26 moves, at least partly, in a direction perpendicular to the long axis of the detected area (z-direction) it causes successive columns of reflective and non-reflective patches to pass through the detected area alternating with the gaps between the successive rings. The reflected light is averaged over the detection region. As plunger element 26 moves, a signal, proportional to the average reflected energy, is output by optical pickup 17a. The signal is responsive, primarily, only to movement in the z-direction. Movement in the φ-direction does not cause the signal to vary significantly because of the shape of the region and its alignment with grid scale 11c. The situation is similar with regard to φ-direction movement and z-direction optical pickup 12a.

Figure 1B:
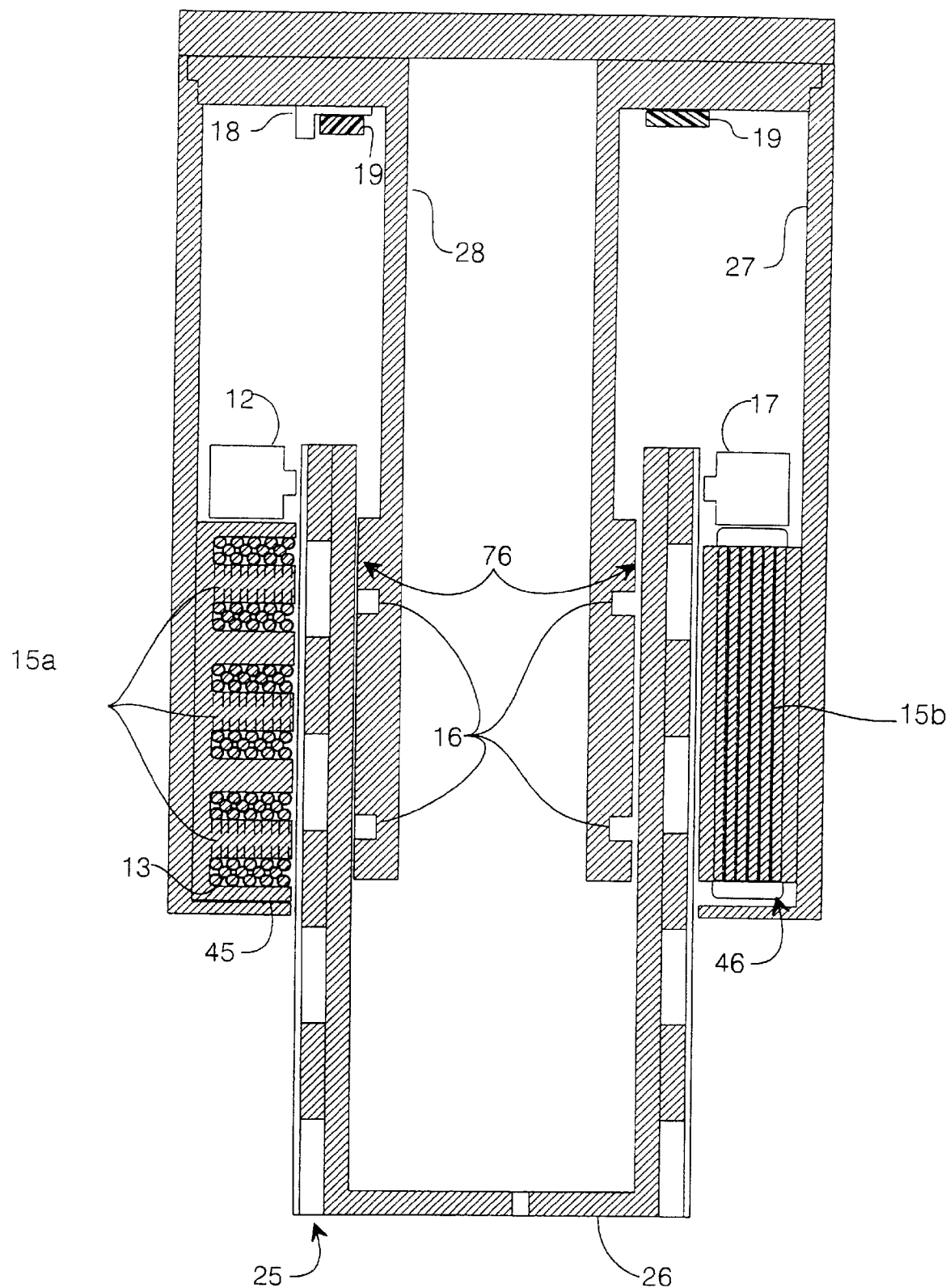
FIG. 1b is a cross-section of the rotary-linear actuator of FIG. 1a in which the plunger shown in a substantially extended position.
Figure 2A:
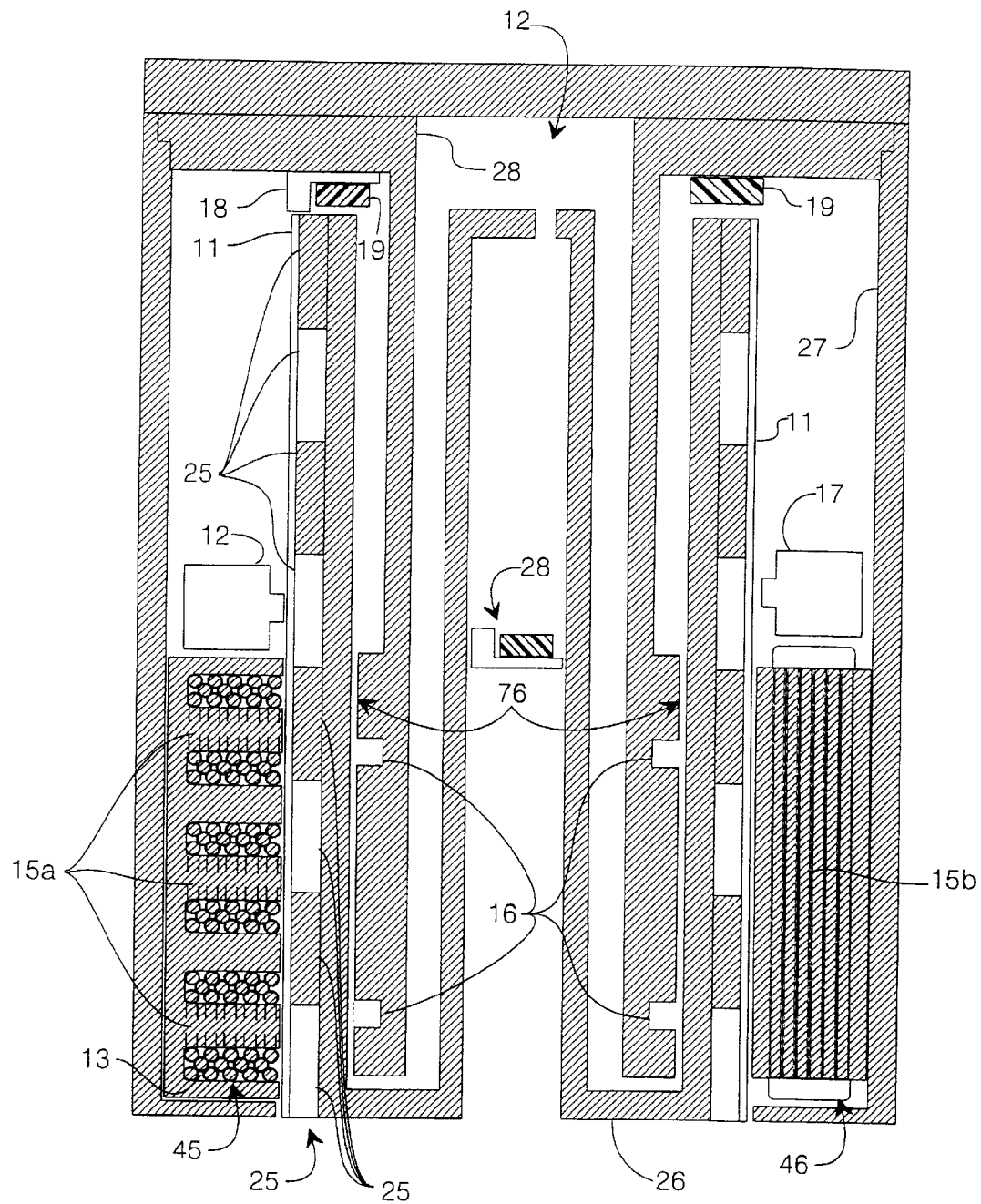
FIG. 2a is a cross-section of a rotary-linear actuator, according to another embodiment of the invention, in which a plunger is shown in a substantially retracted position.
Figure 2B:
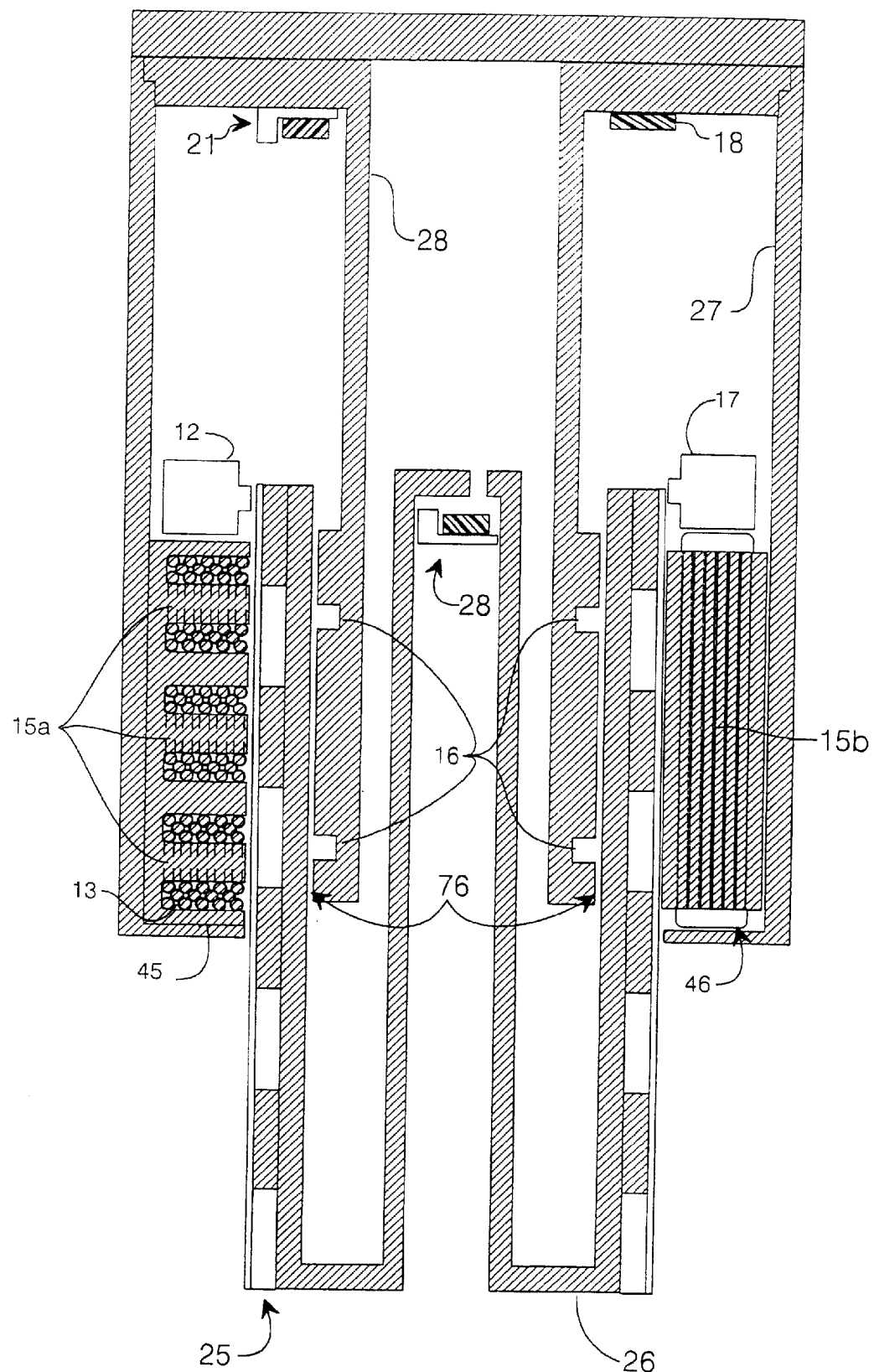
FIG. 2b is a cross-section of the rotary-linear actuator of FIG. 2a in which the plunger shown in a substantially extended position.

Travel of plunger element 26 is limited in the retracted direction (the direction moved by plunger element 26 in going from the position shown in FIG. 1b to the position shown in FIG. 1a) by vertical stops 19 and a limit switch 18. Suitable means may be provided (not shown) for limiting travel in the extension direction (the direction moved by plunger element 26 in going from the position shown in FIG. 1a to the position shown in FIG. 1b). A variation on the configuration of FIGS. 1a and 1b, shown in FIGS. 2a and 2b, permits an extension-direction stop and limit switch assembly 28 to be affixed to motor support 27 and located at the center of plunger element 26 (Note that stop and limit switch assembly's support structure is not shown, but could be provided in a number of ways, such as by attaching it to a stalk running through a center hole in the hollow center column portion of plunger assembly 26).

Figure 3A:
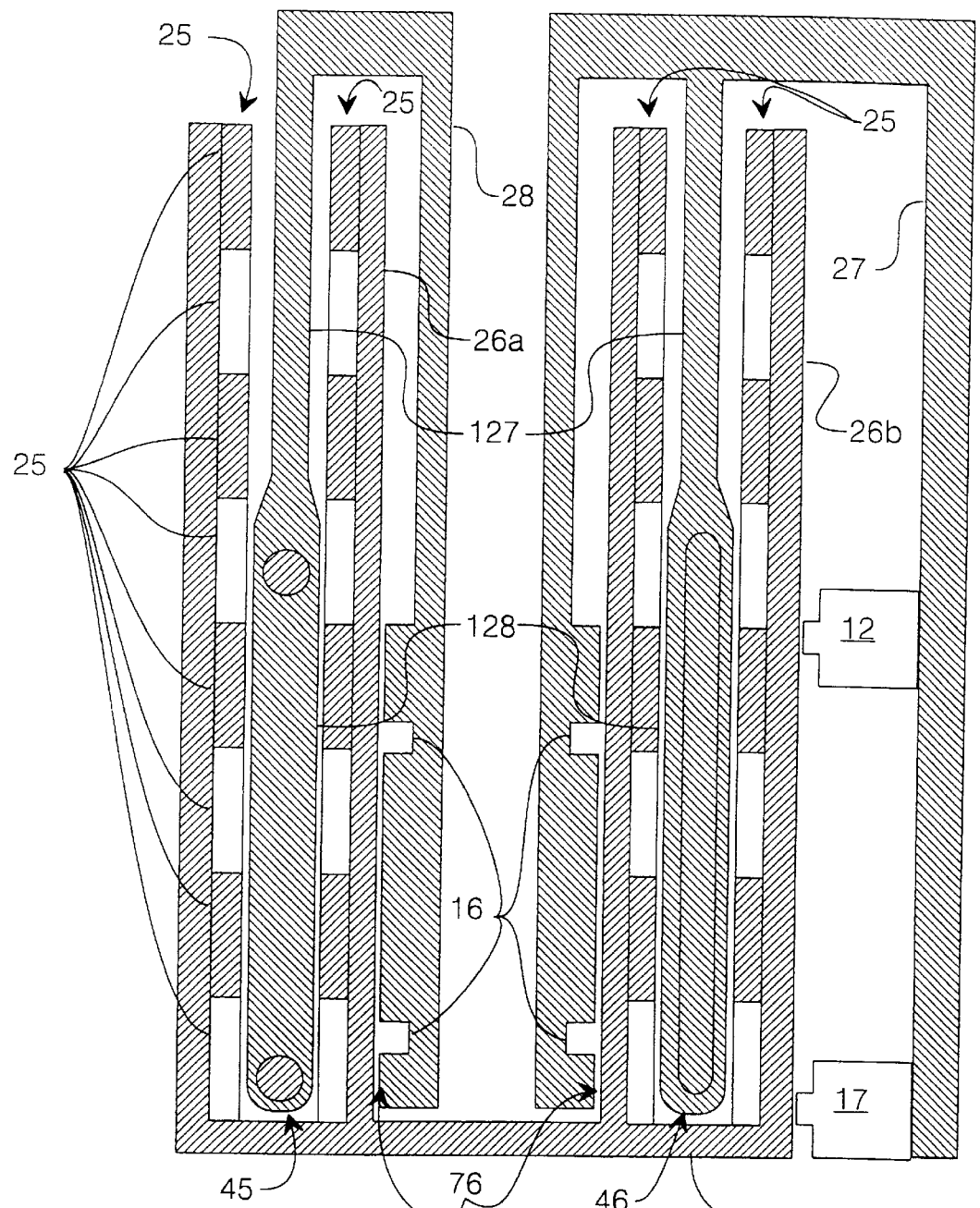
FIG. 3a is a cross-section of a rotary-linear actuator, according to still another embodiment of the invention, in which a plunger is shown in a substantially retracted position.
Figure 3B:
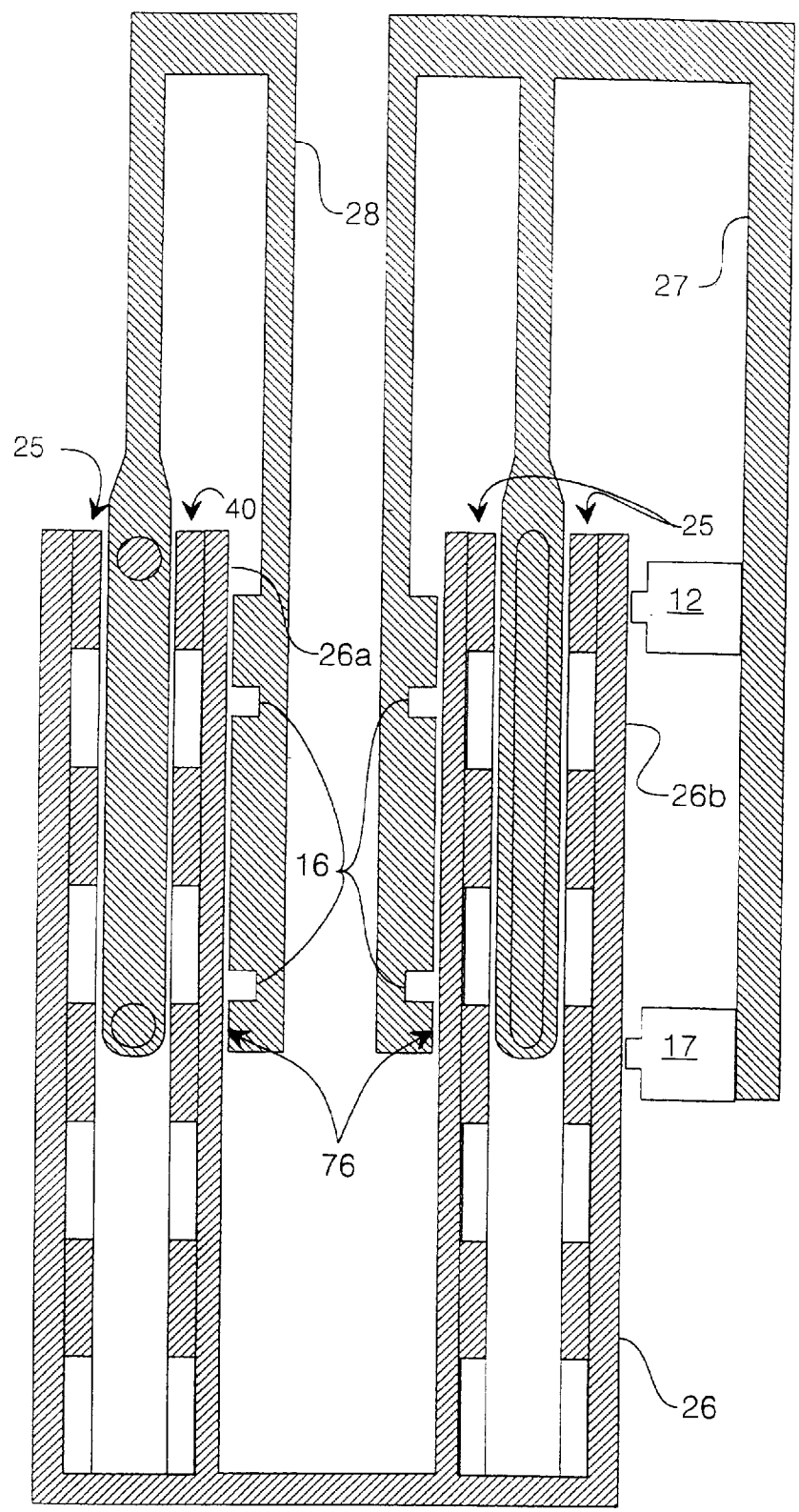
FIG. 3b is a cross-section of the rotary-linear actuator of FIG. 3a in which the plunger shown in a substantially extended position.
Figure 8:
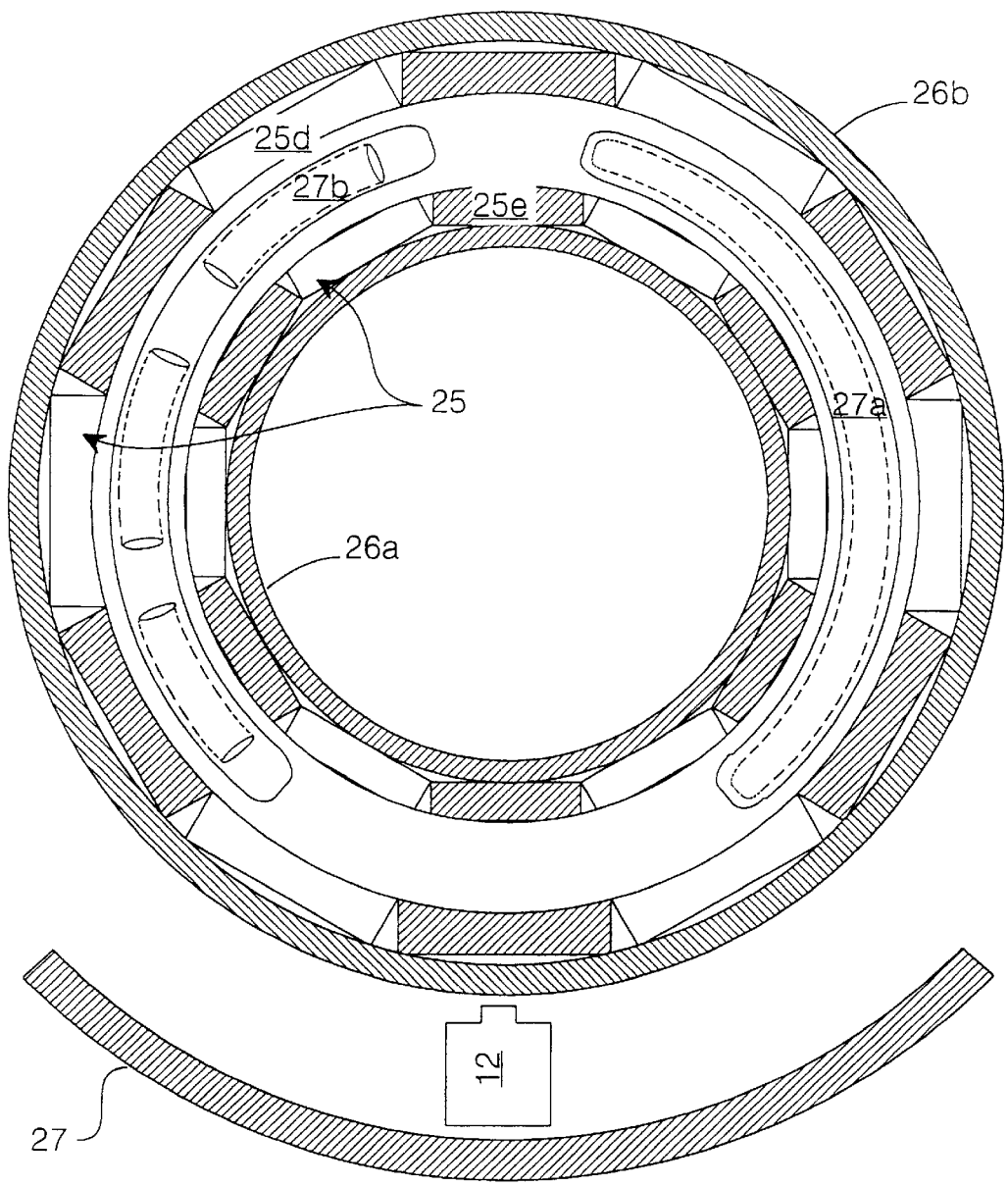
FIG. 8 is a cross section view of the embodiment of FIGS. 3a and 3b.

Referring to FIGS. 3a, 3b, and 8 according to another embodiment of the invention two sets of magnets 25 are affixed to concentric inner and outer cylindrical portions 26a and 26b of plunger element 26. Air bearing 76 supports inner cylindrical portion 26a. The coils that generate the changing magnetic fields that interact with the fields generated by the two sets of magnets 25 are contained in z and φ motors (shown in FIG. 8) embedded in a motor cylinder 128 supported by a motor support cylinder 127. The z and φ motor coils are arranged similarly to the arrangement depicted in FIG. 7a surrounded by two concentric cylindrical arrays of magnets. However, in the embodiments shown no laminations are employed—the coils are embedded in resin alone. The fields generated by z and φ motors 27a and 27b interact with the inner and outer sets of magnets 25e and 25d. So that there is consistent response and maximum power at all rotational positions of plunger element 26, the inner (25e in FIG. 8) and outer sets of magnets (25d in FIG. 8) are sized to maintain rotational symmetry.

In the embodiment of FIGS. 3a and 3b, an encoder scale (not shown), identical to encoder scale 11, is affixed to the outer cylindrical surface of outer cylindrical portion 26b of plunger element 26. Optical pickups 12 and 17 are located on motor support 27.

Figure 3C:
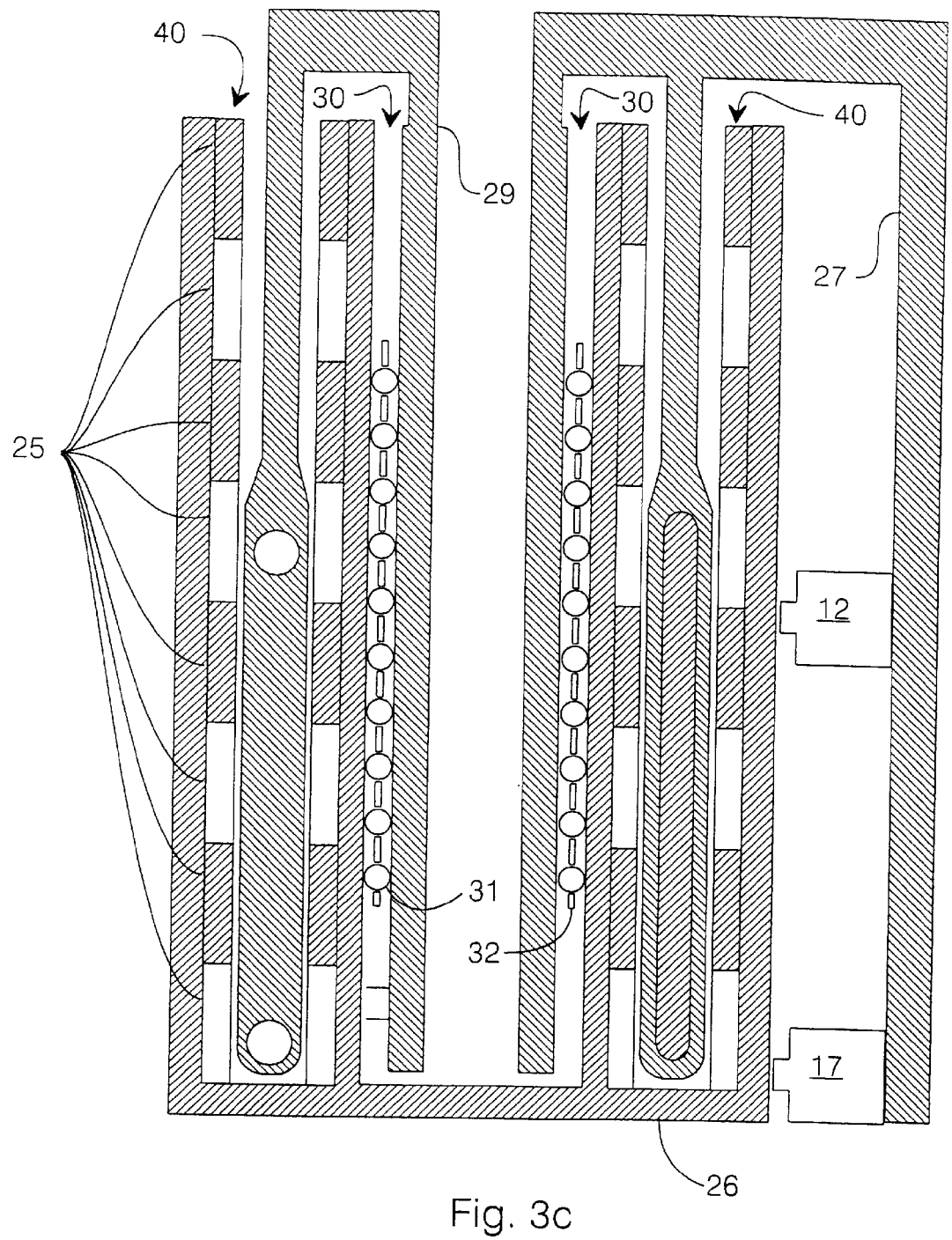
FIG. 3c is a cross-section of rotary-linear actuator similar to that of FIGS. 3a and 3b, but in which the air bearing supporting the plunger is replaced with a bushing with ball-bearings capable of accommodating axial and tangential movement.

Referring to FIG. 3c, an alternative way of supporting plunger element 26 with respect to motor support 27 is to use a cylindrical bushing 30 with ball bearings 31 held in a cylindrical cage 32. Bushing 30 is applicable to all of the embodiments described above and others. Ball bearings 31 are selected in size to develop a proper pre-load. The surfaces adjacent ball bearings 31 may be hardened for durability and precision.

Referring to FIGS. 4a and 4b, to manufacture plunger element 26 with magnets 25, magnets 25 are attached with adhesive to plunger element 27 and coated with epoxy 26f. After epoxy 26f hardens, plunger 27 is machined to form a precision round surface. The above procedure, adapted according to conventional machine shop practice, can be applied to all the embodiments described, and others. For example, the embodiment shown in FIG. 8 requires a precise inside surface of magnets 25d, on outer cylindrical portion 26b. These magnets face inwardly but could be assembled with epoxy and machined as described above to produce a clean cylindrical inside surface.

Figure 6B:
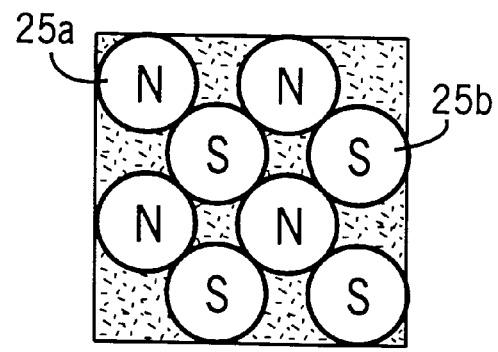
FIG. 6b shows a planar projection of the magnet array attached to the plunger element or a base according to another embodiment of this feature of the invention.
Figure 6C:
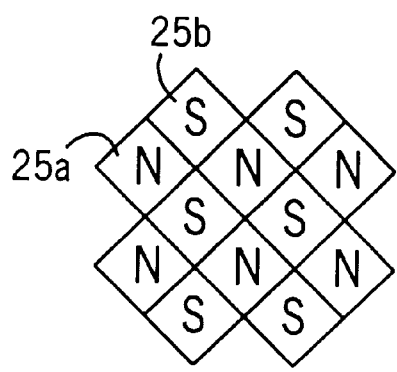
FIG. 6c shows a planar projection of the magnet array attached to the plunger element or a base according to still another embodiment of this feature of the invention.

Referring to FIGS. 6a, 6b, and 6c, note that although in the embodiments described above, magnet 25 arrays with 50% packing density (FIG. 6a) are used, other arrangements are possible. For example, magnets 25 could be round and arranged in a pattern such as that of FIG. 6b or magnets 25 could be diamond shaped and arranged as shown in FIG. 6c. The alternative arrangements shown in FIGS. 6b and 6c have different torque characteristics than that of FIG. 6a which may be desirable for a rotary-linear actuator in specific applications. For example, the arrangement of FIG. 6c with a coil of very narrow width can achieve high peak torque. With a wider coil, it is characterized by low cogging. Peak torque of the arrangement of FIG. 6b is also potentially greater than that of the arrangement of FIG. 6a, depending on the coil width.

Figure 9:
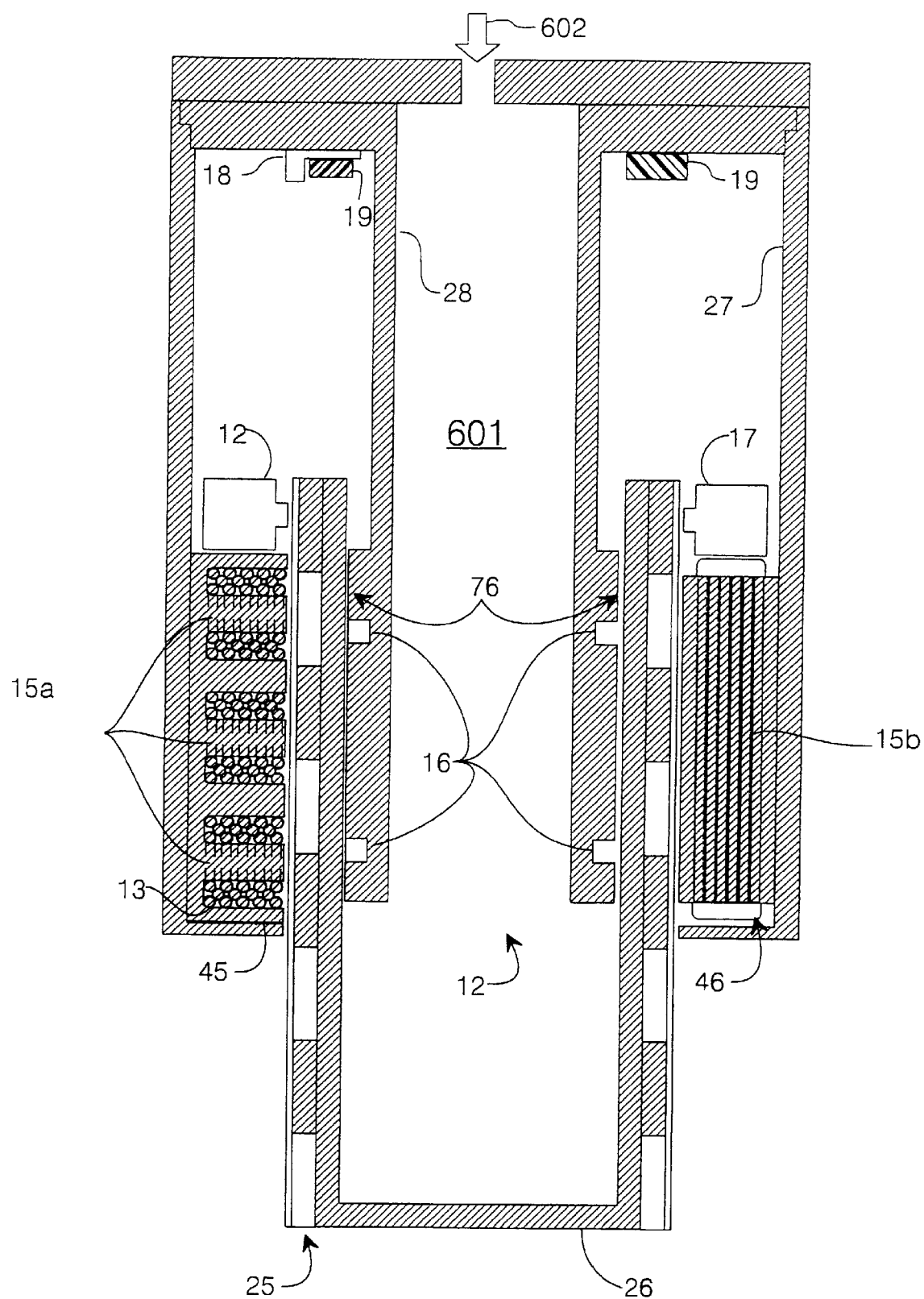
FIG. 9 is a cross section view of an embodiment of the invention having a preferred type of air-cylinder weight compensation system.

Referring to FIG. 9, to avoid loss of potential power and excess motor heat, the weight of plunger element 26 and tools or work-pieces mounted thereon could be compensated for by means of an integral air cylinder 601 formed by sealing the concentric space between motor support 27 and plunger element 26. Connected to a pressure-regulated source of air 602, vacuum or pressure is applied generating a net force on plunger element 26. This source of force could be used to compensate for the weight of a tool or workpiece or other fixture attached to plunger element 26. Alternatively this external force could be used in the operation to which the invention is applied, for example, applying an axial force to a screwdriver. Leaks due to the air bearing (or roller bushing) could be compensated for by the air supply.

Another possible way to make a pressure- or vacuum-augmented version of the rotary-linear actuator is to use a separate sealed air-operated piston/cylinder device (not shown) connected between motor support 27 and plunger element 26 inside the space labeled 601. In addition, note that fluids other than air could also be used to achieve a similar effect, for example, hydraulic fluid could be used instead of air.

Although in the embodiments described, a plunger has permanent magnets and is internally arranged in a motor support, the invention can readily be changed by placing the motors on the plunger element and the permanent magnets on the motor-supporting elements as in the above embodiments. Likewise, the optical pickups could be placed on the plunger element and the scales on the motor support rather than the other way around as shown in the preferred embodiments. In addition, other variations are possible such as providing a single long pillar lined with permanent magnets and a cylindrical motor element with two coaxial open ends. The latter would provide any degree of linear travel required. The encoders would be carried on the motor element and the pillar would have a grid scale on its outer surface. Many other variations are possible. These alternatives are considered to fall within the bounds of at least some of the claims recited below.

Also, although in the embodiments described above, the magnets and coils are arranged so that one set of coils produces forces only in the φ direction (perpendicular to the axis of rotary movement) and another set of coils produces forces only in the direction parallel to the axis of rotary movement, it is recognized that other arrangements are possible. For example, the magnets and coils can be arranged so that each coil, or set of coils, produces forces having both axis-parallel and axis-perpendicular components. Such variations are considered to be within the scope of the invention.

Although only a single or few exemplary embodiments of this invention have been described in detail above, those skilled in the art will readily appreciate that many modifications are possible in the exemplary embodiment(s) without materially departing from the novel teachings and advantages of this invention. Accordingly, all such modifications are intended to be included within the scope of this invention as defined in the following claims. In the claims, means-plus-function clauses are intended to cover the structures described herein as performing the recited function and not only structural equivalents but also equivalent structures. Thus although a nail and screw may not be structural equivalents in that a nail relies entirely on friction between a wooden part and a cylindrical surface whereas a screw's helical surface positively engages the wooden part, in the environment of fastening wooden parts, a nail and a screw may be equivalent structures.

What is claimed is:

1. A three-dimensional permanent magnet linear actuator comprising:

a first cylinder having a first axis;

a first plurality of permanent magnets affixed in a first pattern on said first cylinder;

said first pattern being an axial-circumferential array with alternating magnetic polarities;

a second cylinder fittable with said first cylinder;

a bearing means between said first and second cylinders to permit for maintaining a concentricity of said first and second cylinders and a freedom of relative linear movement of said first and second members along, and relative rotation of said first and second members about, a common axis of said first and second members;

a first plurality of coils on said second cylinder facing said first plurality of permanent magnets;

said first plurality of coils including at least a first coil wound and controllable to interact with said first plurality of permanent magnets to urge said first cylinder in said axial direction, and at least a second coil wound and controllable to urge said first cylinder in said circumferential direction;

one of said at least first and second coils has a long axis that curves around, and is substantially perpendicular to, said first axis; and an other of said at least first and second coils has a long axis that is substantially parallel to said first axis.

2. A linear actuator according to claim 1, further comprising:

said first cylinder being inside said second cylinder;

a third cylinder fitted outside said second cylinder;

said third cylinder having a second plurality of permanent magnets affixed in a second axial-circumferential array with second alternating magnetic polarities; and said magnetic polarities of said second plurality of permanent magnets being being disposed in said second axial-circumferential array to add to urging of said first cylinder of said second cylinder.

* * * * *